United States Patent
Wang et al.

(10) Patent No.: US 7,171,286 B2
(45) Date of Patent: Jan. 30, 2007

(54) HEALTHCARE TELE-ROBOTIC SYSTEM WITH A ROBOT THAT ALSO FUNCTIONS AS A REMOTE STATION

(75) Inventors: Yulun Wang, Goleta, CA (US); Charles S. Jordan, Santa Barbara, CA (US); Keith Phillip Laby, Santa Barbara, CA (US); Jonathan Southard, Santa Barbara, CA (US); Marco Pinter, Santa Barbara, CA (US)

(73) Assignee: InTouch Technologies, Inc., Goleta, CA (US)

( * ) Notice: Subject to any disclaimer, the term of this patent is extended or adjusted under 35 U.S.C. 154(b) by 107 days.

(21) Appl. No.: 10/660,886

(22) Filed: Sep. 12, 2003

(65) Prior Publication Data

US 2004/0167668 A1    Aug. 26, 2004

Related U.S. Application Data

(60) Provisional application No. 60/449,666, filed on Feb. 24, 2003.

(51) Int. Cl.
*G06F 19/00* (2006.01)

(52) U.S. Cl. ............ 700/248; 700/245; 700/247; 700/251; 700/257; 700/258; 700/259; 700/260; 700/261; 700/262; 700/264; 318/568.11; 318/568.12; 318/568.13; 318/568.16; 318/568.21; 318/568.25; 606/1; 606/102; 606/130; 606/139; 600/117; 600/118; 600/407; 600/426; 600/429; 600/587; 600/595; 901/1; 901/2; 901/27

(58) Field of Classification Search ......... 318/568.21, 318/568.22, 568.25, 568.11, 568.12, 568.13, 318/568.16; 600/102–103, 109, 117–118, 600/407, 426, 429, 587, 595; 901/1–2, 27, 901/36; 700/131–132, 245–248, 251, 253, 700/257–262, 264; 606/1, 102, 130, 139
See application file for complete search history.

(56) References Cited

U.S. PATENT DOCUMENTS

| 5,374,879 A | 12/1994 | Pin et al. |
| 5,802,494 A * | 9/1998 | Kuno ............ 705/2 |
| 5,959,423 A | 9/1999 | Nakanishi et al. |

(Continued)

FOREIGN PATENT DOCUMENTS

CA    2289697 A1    11/1998

OTHER PUBLICATIONS

☐☐Mack, Minimally invasive and robotic surgery, 2001, IEEE, pp. 568-572.*

(Continued)

*Primary Examiner*—Thomas Black
*Assistant Examiner*—McDieunel Marc
(74) *Attorney, Agent, or Firm*—Ben J. Yorks; Irell & Manella LLP

(57) ABSTRACT

A robotic system that includes a plurality of robots that are linked to a plurality of remote stations. The robots have an input device and software that allows control of another robot. This allows an operator in close physical proximity to a robot to operate another robot. Each robot can be either a master or slave device.

40 Claims, 10 Drawing Sheets

U.S. PATENT DOCUMENTS

| | | |
|---|---|---|
| 6,259,806 B1 | 7/2001 | Green |
| 6,292,713 B1 | 9/2001 | Jouppi et al. |
| 6,346,950 B1 | 2/2002 | Jouppi |
| 6,369,847 B1 | 4/2002 | James et al. |
| 6,430,471 B1 | 8/2002 | Kintou et al. |
| 6,438,457 B1* | 8/2002 | Yokoo et al. ............... 700/245 |
| 6,463,361 B1 | 10/2002 | Wang et al. |
| 6,491,701 B2 | 12/2002 | Tierney et al. |
| 6,496,099 B2 | 12/2002 | Wang et al. |
| 6,522,906 B1* | 2/2003 | Salisbury et al. ........... 600/407 |
| 6,535,793 B2 | 3/2003 | Allard |
| 6,549,215 B2 | 4/2003 | Jouppi |
| 6,587,750 B2* | 7/2003 | Gerbi et al. ................ 700/245 |
| 6,594,552 B1* | 7/2003 | Nowlin et al. .............. 700/260 |
| 6,684,129 B2* | 1/2004 | Salisbury et al. ........... 700/245 |
| 6,799,065 B1* | 9/2004 | Niemeyer ................... 600/407 |
| 6,839,612 B2* | 1/2005 | Sanchez et al. ............. 700/245 |
| 6,852,107 B2* | 2/2005 | Wang et al. ................... 606/1 |
| 2001/0054071 A1 | 12/2001 | Loeb |
| 2002/0027597 A1 | 3/2002 | Sachau |
| 2002/0057279 A1 | 5/2002 | Jouppi |
| 2002/0058929 A1 | 5/2002 | Green |
| 2002/0063726 A1 | 5/2002 | Jouppi |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0183894 A1 | 12/2002 | Wang et al. |
| 2003/0050733 A1 | 3/2003 | Wang et al. |
| 2003/0114962 A1* | 6/2003 | Niemeyer ................... 700/245 |
| 2003/0135203 A1* | 7/2003 | Wang et al. ................... 606/1 |
| 2003/0144649 A1* | 7/2003 | Ghodoussi et al. ............ 606/1 |
| 2003/0151658 A1 | 8/2003 | Smith |
| 2003/0220541 A1* | 11/2003 | Salisbury et al. ........... 600/101 |
| 2005/0038416 A1* | 2/2005 | Wang et al. ................... 606/1 |

OTHER PUBLICATIONS

Davies, Robotics in minimilly invasive surgery, 1995, Internet, pp. 5/1-5/2.*

Stoianovici et al., Robotic tools for minimally invasive urologic surgery, 2002, Internet, 1-17.*

Tendick et al., Human-machine interfaces for minimally invasive surgery, 1997, IEEE, pp. 1-6.*

Schaaf, Robotic surgery: The future in now, 2001, Internet, pp. 1-11.*

Student BMJ, Robotics in surgery, 2002, Internet, pp. 1-4.*

Stephenson, Dr. robot tested at Hokins, 2003, Internet, p. 1-2.*

CNN.com/Technology, Paging R. Robot: Machine helps doctors with patients, 2003, Internet, 1-3.*

Roland Piquepaille's Technology Trens, How new technologies are modifying your way of life, 2003, Internet, p. 1-2.*

Mobile Robotics Research Group, Edinburgh, 2000, Internet, p. 1-2.*

Paulos et al., "A World Wide Web Telerobotic Remote Environment Browser", http://vive.cs.berkeley.edu/capek, 1995.

* cited by examiner

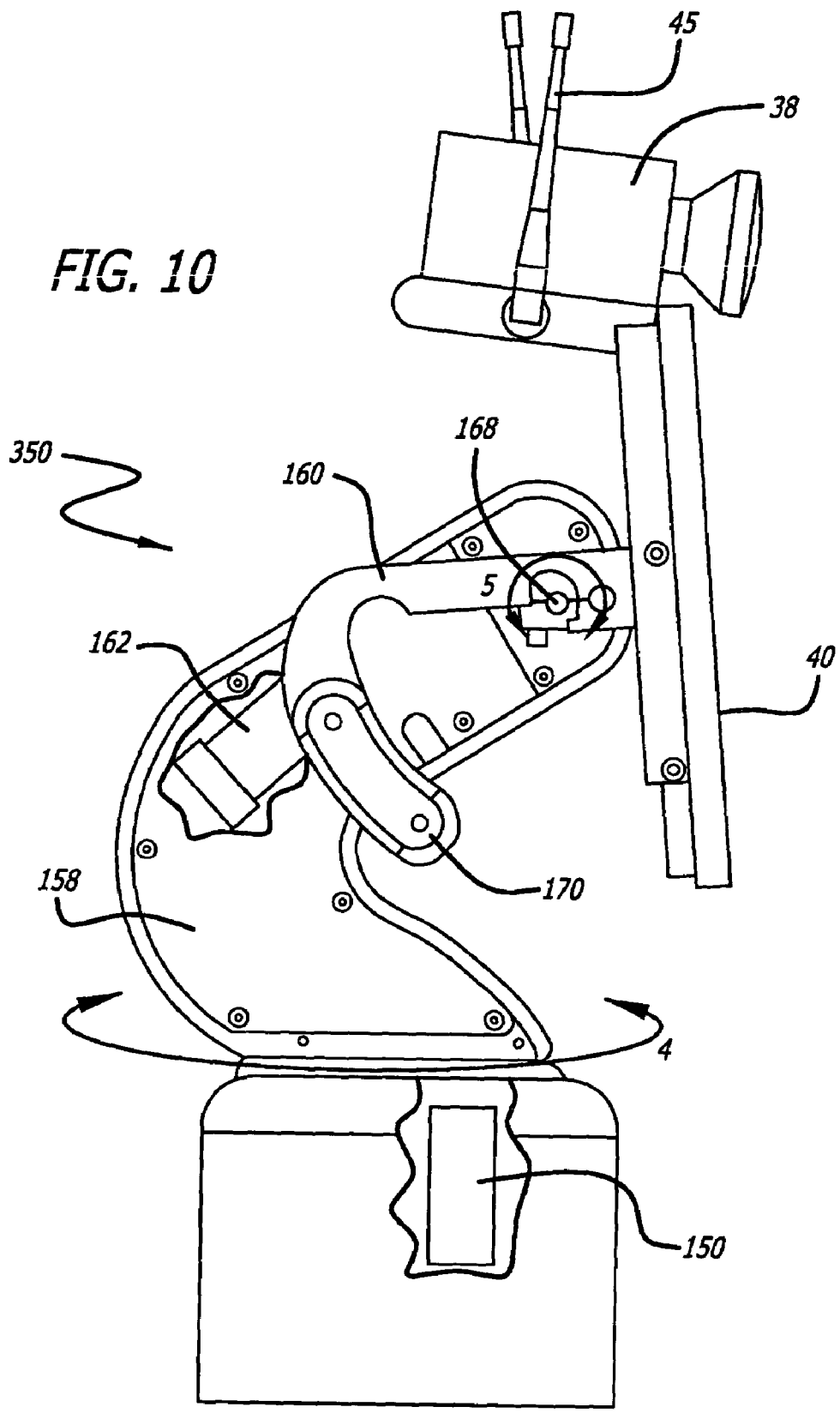

HEALTHCARE TELE-ROBOTIC SYSTEM WITH A ROBOT THAT ALSO FUNCTIONS AS A REMOTE STATION

REFERENCE TO CROSS-RELATED APPLICATIONS

This application claims priority to Provisional Application No. 60/449,666 filed on Feb. 24, 2003.

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Robots have been used in a variety of applications ranging from remote control of hazardous material to assisting in the performance of surgery. For example, U.S. Pat. No. 5,762,458 issued to Wang et.al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The Treviranus patent also discloses embodiments with a mobile platform, and different mechanisms for moving the camera and the monitor.

Publication Application No. US-2003-0050733-A1 discloses a remote robotic system wherein a plurality of remote stations can control a plurality of robotic arms used to perform a minimally invasive medical procedure. Each remote station can receive a video image provided by the endoscope inserted into the patient. Such a system is also being developed by Computer Motion, Inc. under the name SOCRATES. The remote stations are linked to the robotic system by a dedicated communication link.

BRIEF SUMMARY OF THE INVENTION

A mobile robot system that includes a first mobile robot and a second mobile robot. The second mobile robot has an input that allows at operator to control the movement of the first mobile robot.

BRIEF DESCRIPTION OF THE DRAWINGS

FIG. 10 is a side view of a robot head.

DETAILED DESCRIPTION

Disclosed is a robotic system that includes a plurality of robots that are linked to a plurality of remote stations. The robots have an input device and software that allows control of another robot. This allows an operator in close physical proximity to a robot to operate another robot. Each robot can be either a master or slave device.

Figure 1:
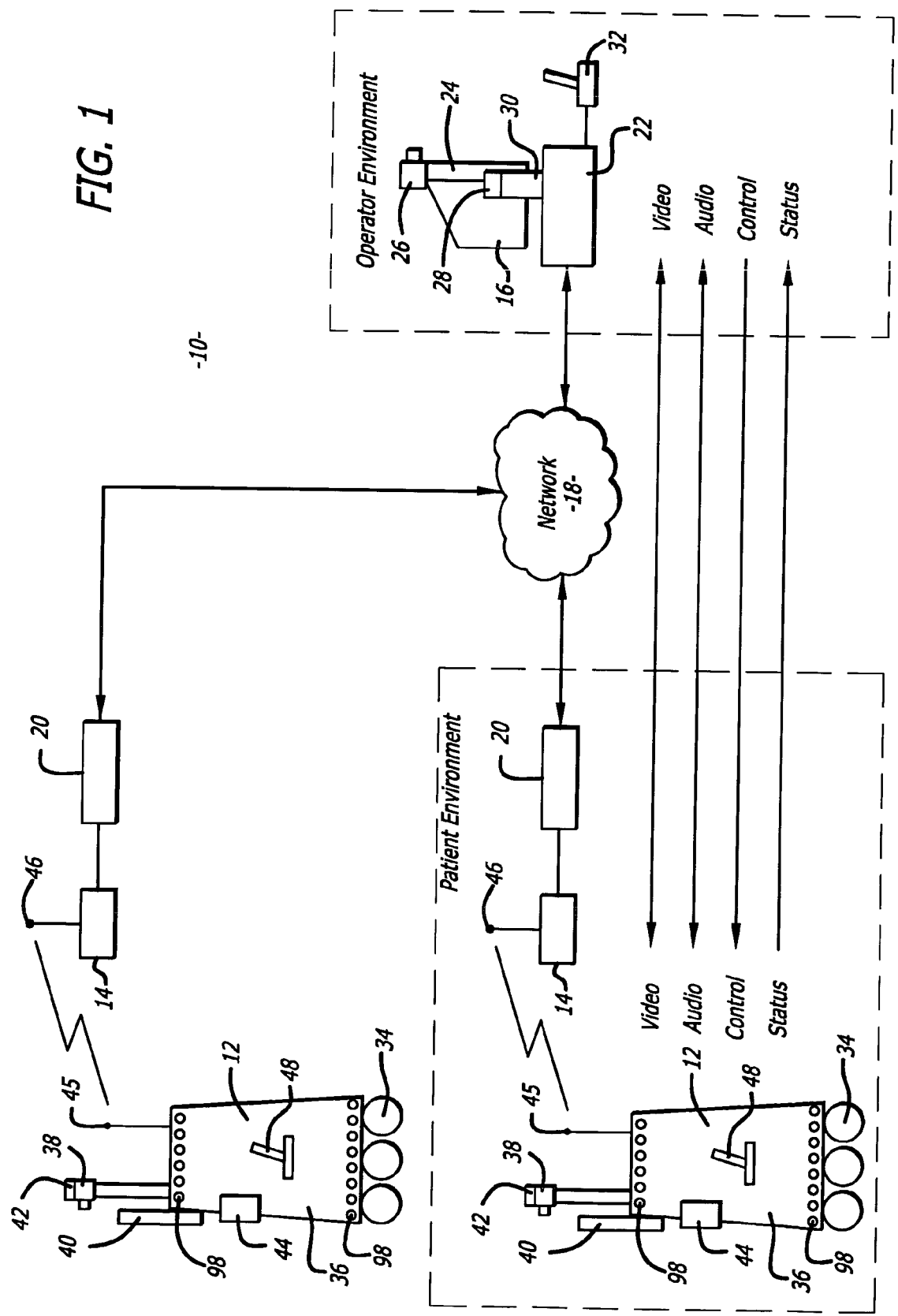
FIG. 1 is an illustration of a robotic system.

Referring to the drawings more particularly by reference numbers, FIG. 1 shows a robotic system 10. The robotic system 10 includes a plurality of robots 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each robot 12 may have an input device 48, such as a joystick that allows an operator to control another robot 12. Although a joystick is shown and described, it is to be understood that the input device 48 may include other means to input control commands such as a keyboard (not shown) mounted to the robot 12, a keyboard (not shown) wirelessly coupled to the robot 12, or a speech recognition interface that receives and interprets audible commands.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
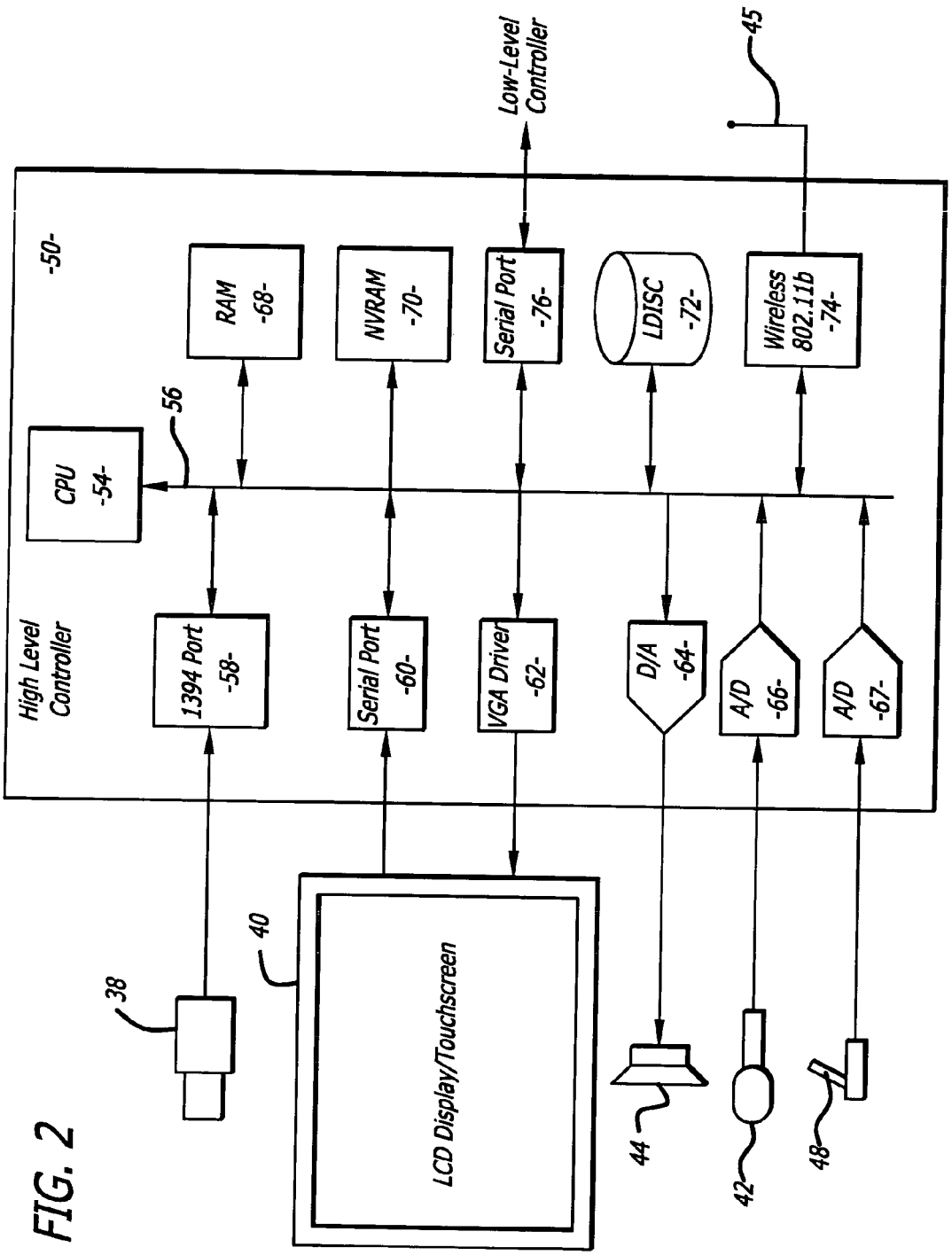
FIG. 2 is a schematic of an electrical system of a robot.
Figure 3:
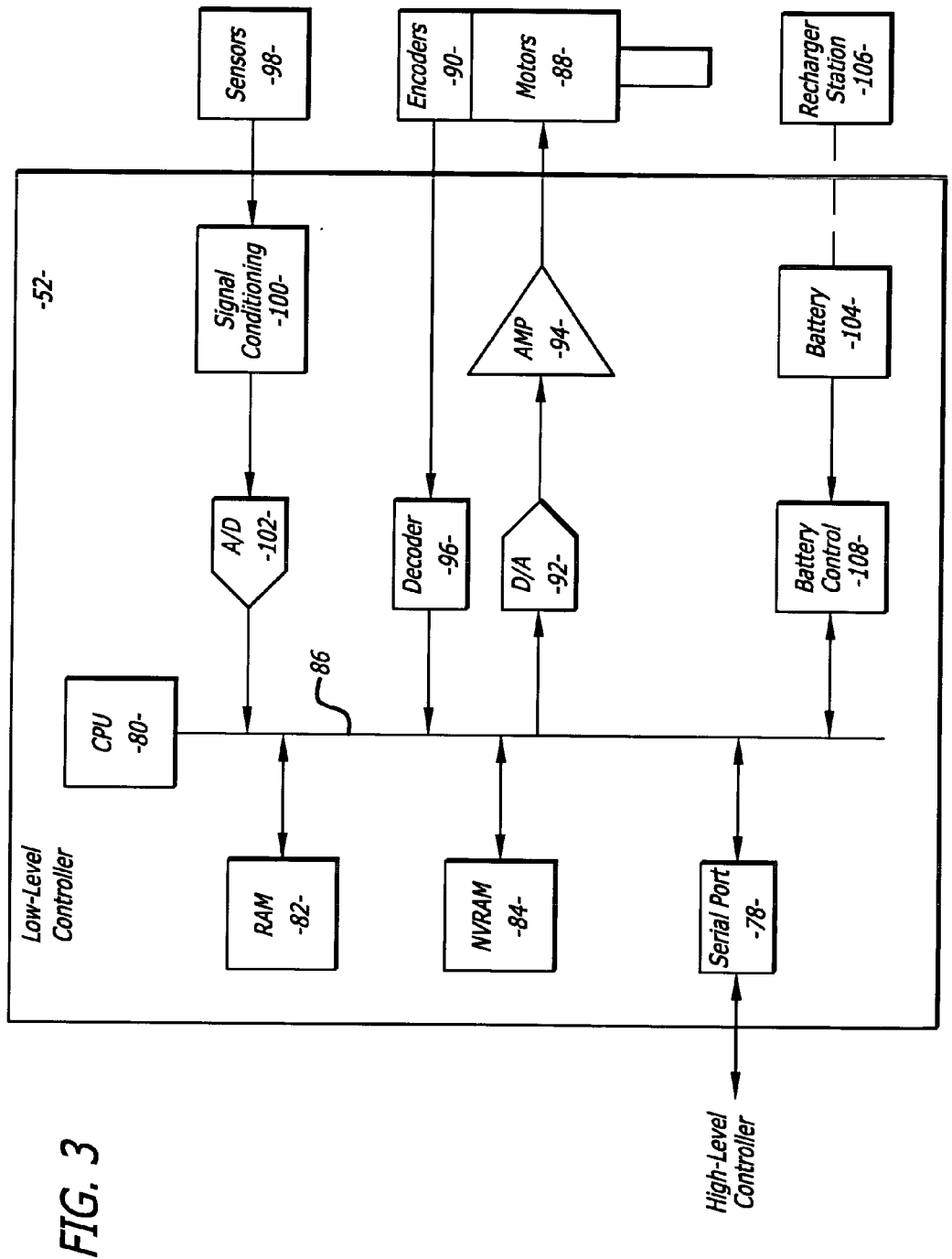
FIG. 3 is a further schematic of the electrical system of the robot.

FIGS. 2 and 3 show an embodiment of a robot 12. Each robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The input device 48 is coupled to the bus by an analog to digital converter 67. Movement of the input device 48 is converted to digital bit string that are processed by controller 50 and transmitted to the base station 14, through the network 18 and to another robot 12. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. Each robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. Each robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
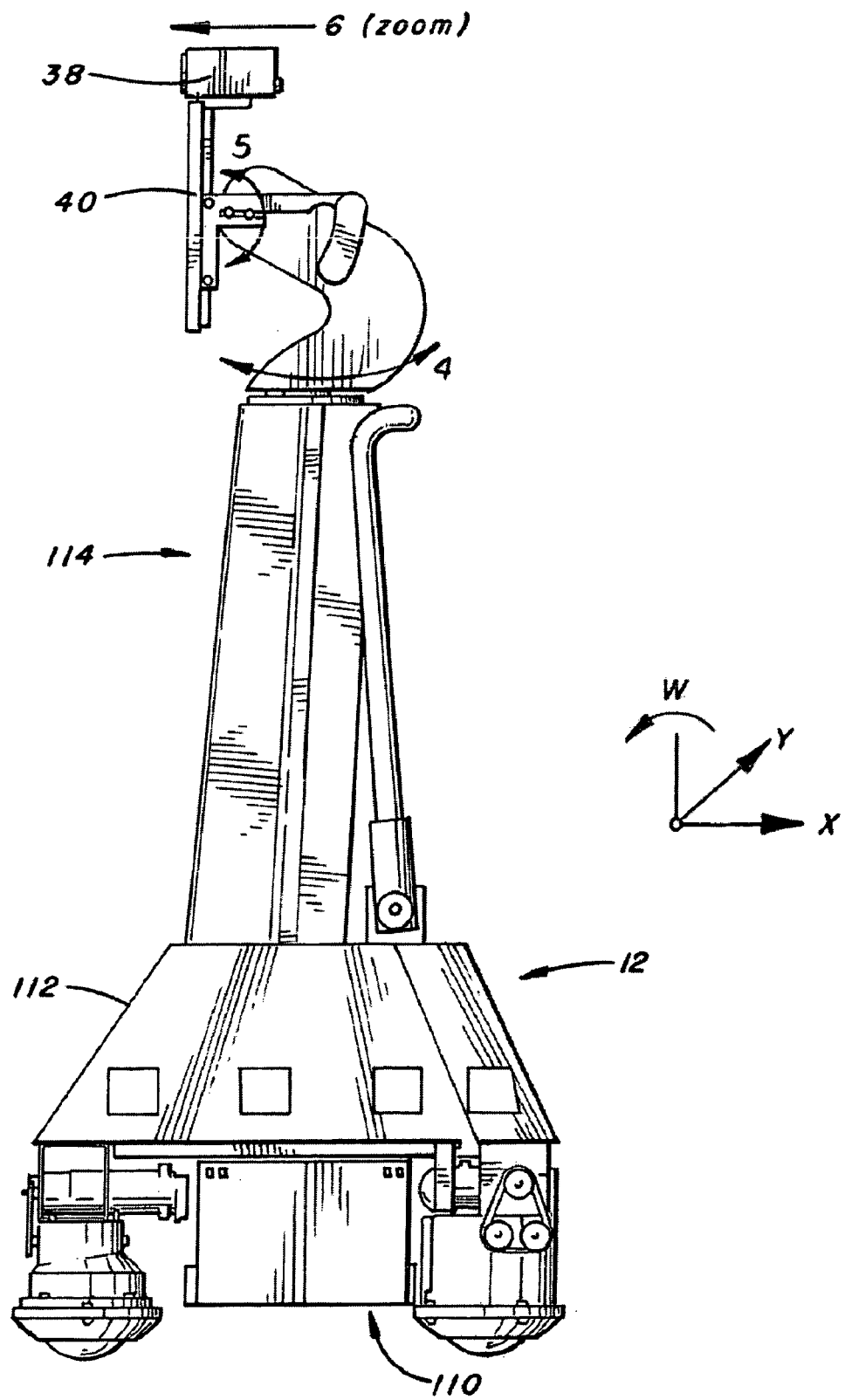
FIG. 4 is side view of the robot.

FIG. 4 shows an embodiment of a robot 12. Each robot 12 may include a holonomic platform 110 that is attached to a robot housing 112. The holonomic platform 110 provides three degrees of freedom to allow the robot 12 to move in any direction.

Each robot 12 may have an pedestal assembly 114 that supports the camera 38 and the monitor 40. The pedestal assembly 114 may have two degrees of freedom so that the camera 26 and monitor 24 can be swiveled and pivoted as indicated by the arrows.

Figure 5:
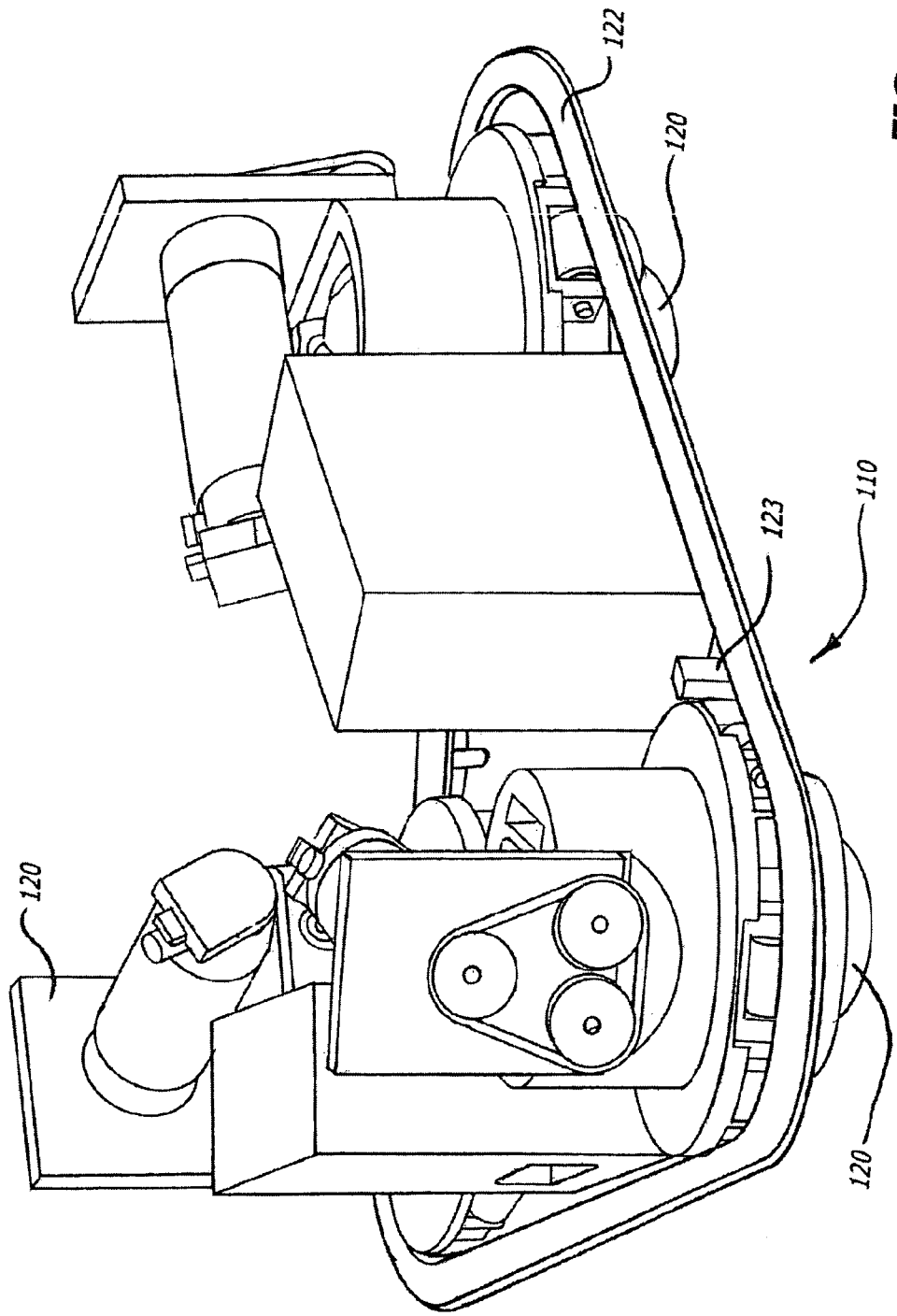
FIG. 5 is a top perspective view of a holonomic platform of the robot.

As shown in FIG. 5 the holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 6:
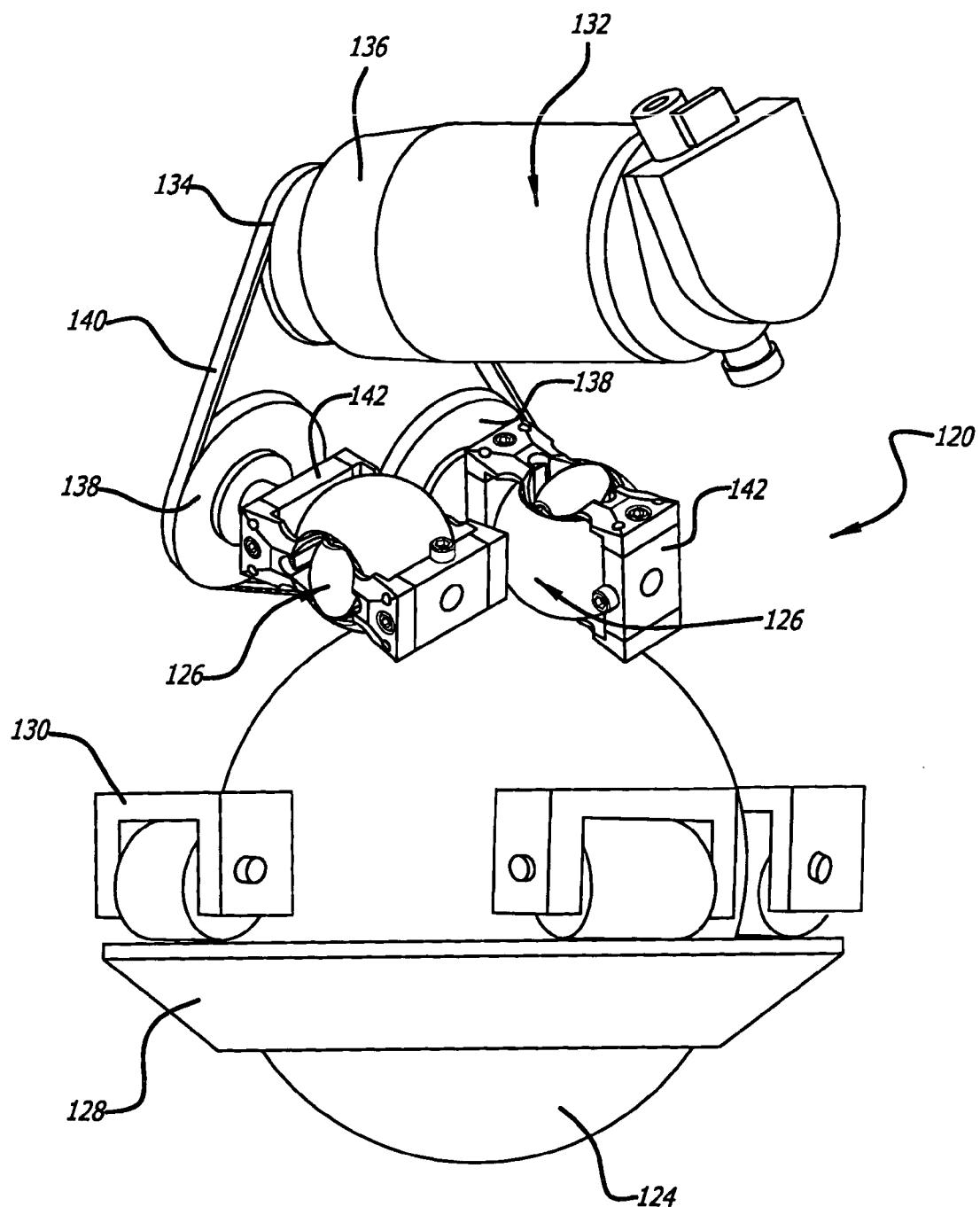
FIG. 6 is a side perspective view of a roller assembly of the holonomic platform.

FIG. 6 shows an embodiment of a roller assembly 120. Each assembly 120 may include a drive ball 124 that is driven by a pair of transmission rollers 126. The assembly 120 includes a retainer ring 128 and a plurality of bushings 130 that capture and allow the ball 124 to rotate in an x and y direction but prevents movement in a z direction.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin and allow orthoganal directional passive movement when one of the other roller assemblies 120 is driving and moving the robot 12.

Figure 7:
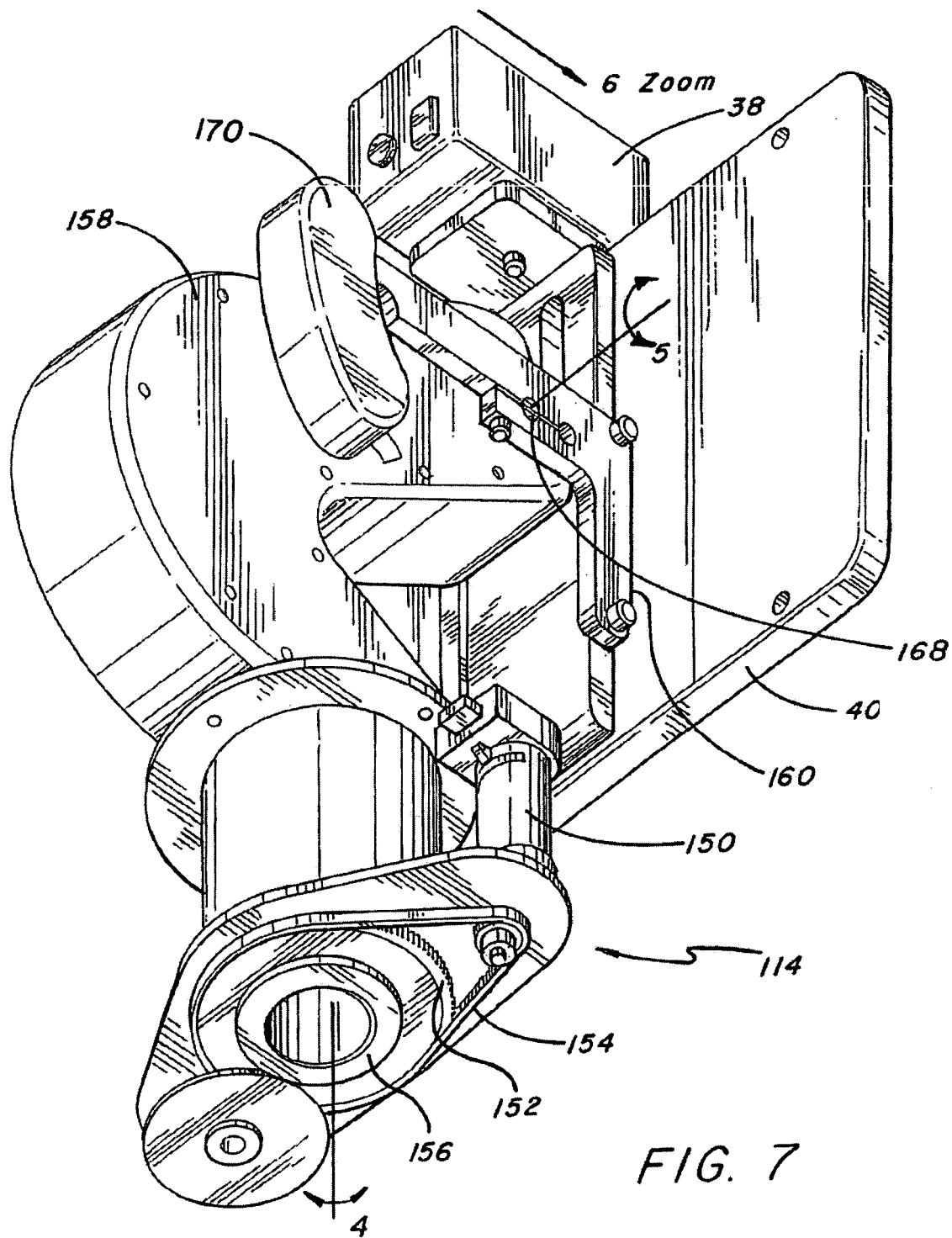
FIG. 7 is a bottom perspective view showing a pedestal assembly of the robot.

As shown in FIG. 7, the pedestal assembly 114 may include a motor 150 that is coupled to a gear 152 by a belt 154. The gear 152 is attached to a sleeve 156. The sleeve 156 is coupled to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

Figure 8:
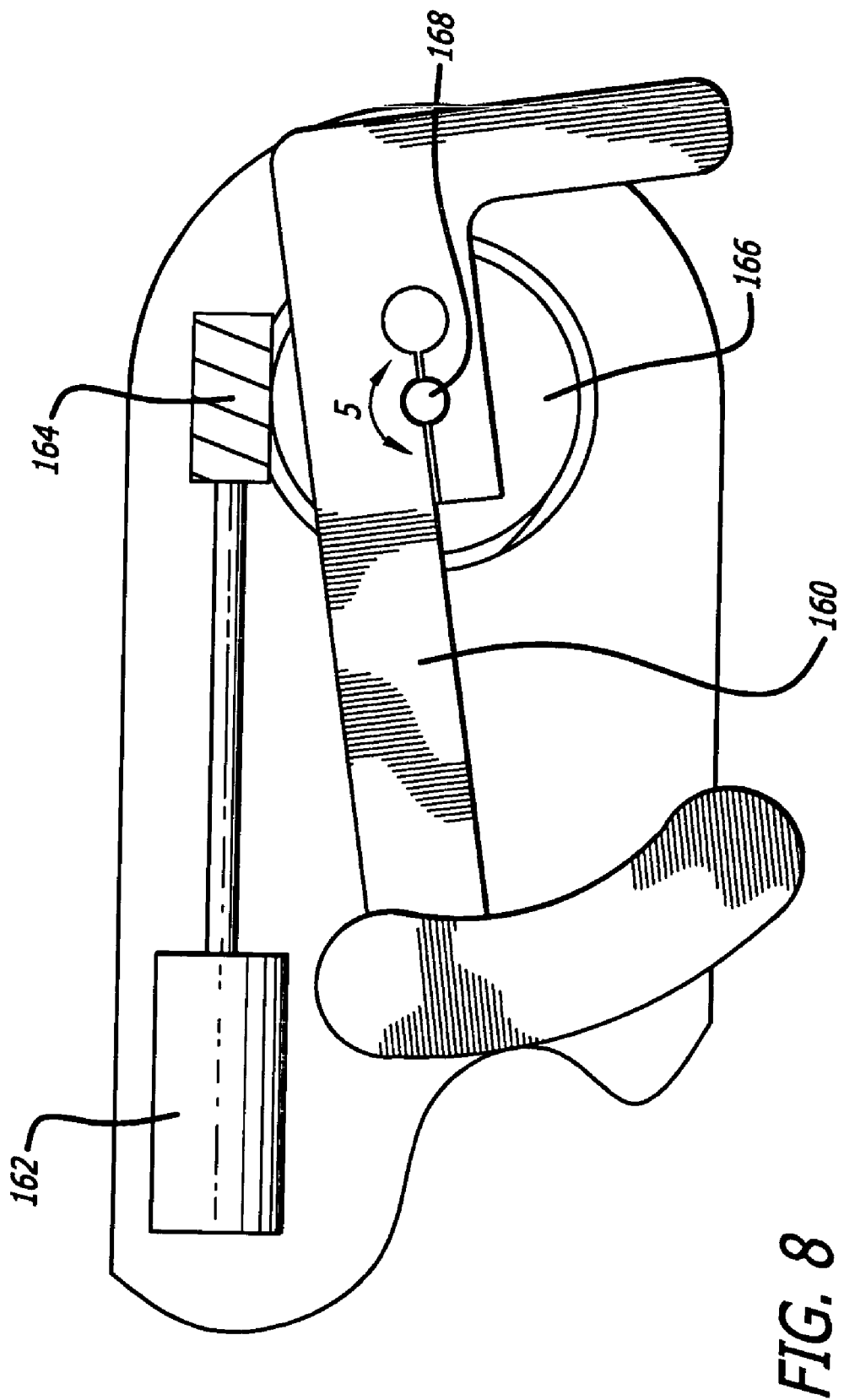
FIG. 8 is a sectional view showing an actuator of the pedestal assembly.

As shown in FIG. 8, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, each robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control station allow for teleconferencing between the patient and the person at the remote station, or another robot.

Each robot 12 can be maneuvered through the home or facility by manipulating the input device 32 at the remote station 16, or through the input device 48 of another robot 12.

Each robot 10 may be controlled by a number of different users at the remote station(s) 16 and/or robot(s) 12. To accommodate for this each robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. These users may provide input from either a remote station or another robot. The robot may override input commands that conflict with robot operation. For example, if the robot runs into a wall, the system may ignore all additional commands to continue in the direction of the wall. A local user is a person who is physically present with the robot. The robot could have an input device that allows local operation. The same input device may also control a different robot.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

Message packets may be transmitted between a robot 12 and a remote station 16 or between robots 12. The packets provide commands and feedback. Each packet may have multiple fields. By way of example, a packet may include an ID field a forward speed field, an angular speed field, a stop field, a bumper field, a sensor range field, a configuration field, a text field and a debug field.

The identification of remote users can be set in an ID field of the information that is transmitted from the remote control station 16 to the robot 12. For example, a user may enter a user ID into a setup table in the application software run by the remote control station 16. The user ID is then sent with each message transmitted to the robot.

Each robot 12 may operate in different modes; an exclusive mode, a sharing mode, or a remote station mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous teleconference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables 1 and 2, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| | | Requesting User | | | | |
|---|---|---|---|---|---|---|
| | | Local | Caregiver | Doctor | Family | Service |
| Current User | Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| | Caregiver | Warn current user | Not Allowed | Warn current user of | Warn current user of | Warn current user of |

TABLE II-continued

| | Requesting User | | | | |
|---|---|---|---|---|---|
| | Local | Caregiver | Doctor | Family | Service |
| | of pending user. Notify requesting user that system is in use. Release control | | pending user Notify requesting user that system is in use Set timeout = 5 m Queue or callback | pending user Notify requesting user that system is in use Set timeout = 5 m | pending user Notify requesting user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16 or another robot 12. The robot 12 validates the key and returns another key to the station 16. The keys are used to encrypt information transmitted in the session.

In the remote station mode, a robot can be used to control another robot. An operator can move the joystick 48 to move the other robot like the joystick 32 of the remote station is used to control a robot. The operator can select a robot of choice through an input device of the master robot. By way of example, the input device may be a touch pad graphical user interface provided by the monitor 40.

Figure 9:
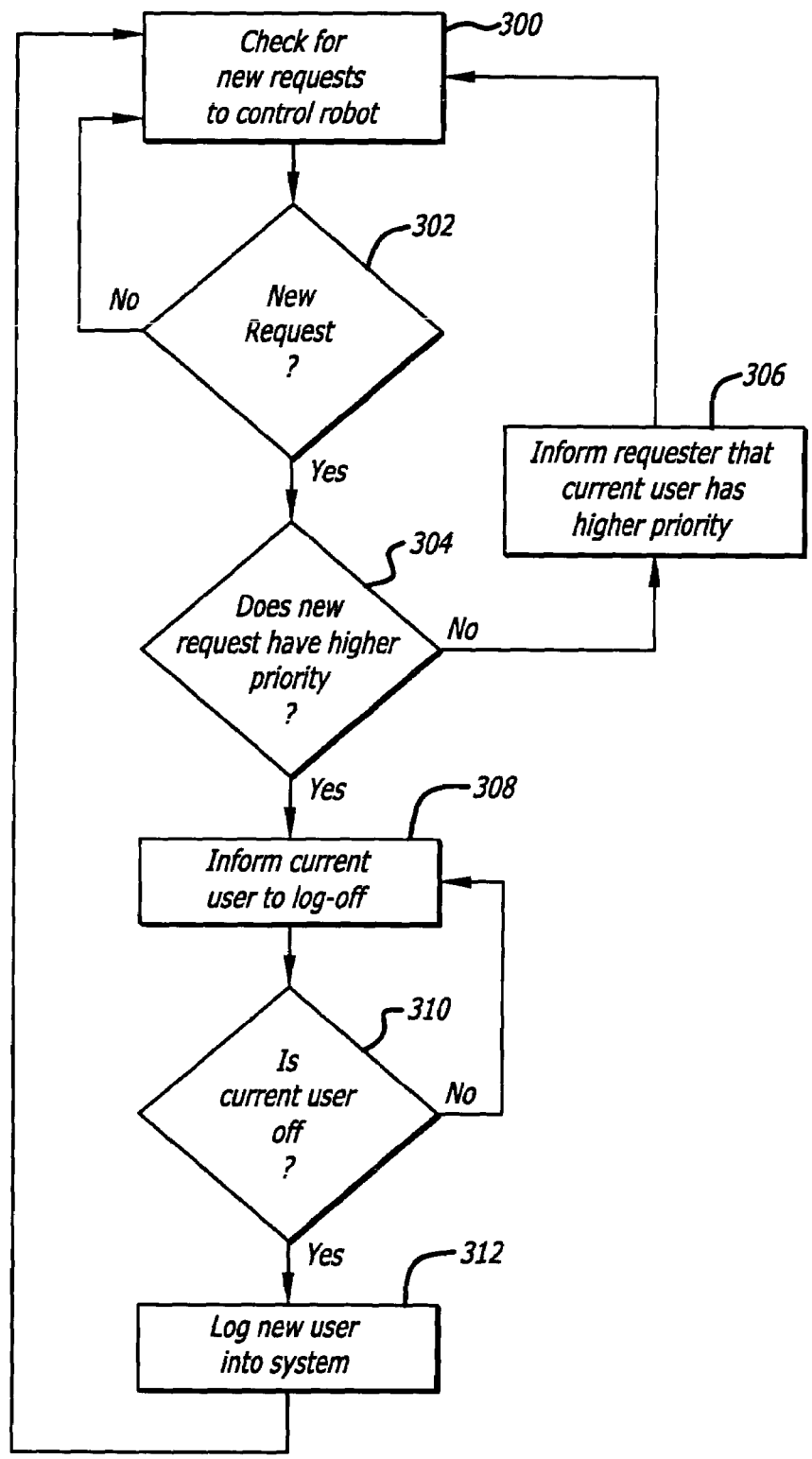
FIG. 9 is a flowchart showing a priority scheme for controlling a mobile robot.

FIG. 9 is a flowchart showing use of the robot 12 as a remote station to control another robot. In decision block 300 an operator at one robot generates an access request to control another robot. This could be done through the monitor interface. The request includes a priority number of the requesting robot. The robot receiving the request determines whether the request is new in decision block 302. If the request is new the robot receiving the request determines whether the requesting robot has a priority higher than a station 16 or other robot 12 that already has access to the robot in decision block 304.

If the requesting robot does not have a higher priority then the robot receiving the request transmits a statement to the requesting robot that access is denied in block 306. If the requesting robot does have higher priority the receiving robot transmits a message to the station or robot with present access, to log-off in block 308. The receiving robot determines whether the present user has logged-off in decision block 310. If the present user has logged-off then the receiving robot allows the requesting robot to log on and control the robot in block 312.

FIG. 10 shows a robot head 350 that can both pivot and spin the camera 38 and the monitor 40. The robot head 350 can be similar to the robot 12 but without the platform 110. The robot head 350 may have the same mechanisms and parts to both pivot the camera 38 and monitor 40 about the pivot axis 4, and spin the camera 38 and monitor 40 about the spin axis 5. The pivot axis may intersect the spin axis. Having a robot head 350 that both pivots and spins provides a wide viewing area. The head 350 may be used with or instead of the mobile robot 12. The head 350 may have an input device (not shown) such as a joystick for controlling another robot.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A mobile robot system, comprising:
    a first mobile robot with a camera and a monitor that move together in at least one degree of freedom; and,
    a second mobile robot that has an input device controlled by a user to control movement of said first mobile robot across a floor surface, said second mobile robot having a camera and a monitor that move together in at least one degree of freedom.

2. The system of claim 1, wherein said first and second mobile robots each include a speaker and a microphone.

3. The system of claim 1, wherein said input device includes a joystick.

4. The system of claim 1, wherein said input device includes a speech interface.

5. The system of claim 1, wherein said first and second mobile robots each include a platform that provides three degrees of freedom.

6. The system of claim 1, further comprising a remote station that has an input device to control said first mobile robot.

7. The system of claim 6, wherein said first mobile robot includes an arbitrator.

8. The system of claim 1, further comprising a wireless base station coupled to said first mobile robot.

9. A mobile robot system, comprising:
a first mobile robot with a camera and a monitor that move together in at least one degree of freedom; and,
a second mobile robot with input means for controlling movement of said first mobile robot across a floor surface that is controlled by a user, said second mobile robot having a camera and a monitor that move together in at least one degree of freedom.

10. The system of claim 9, wherein said first and second mobile robots each include a speaker and a microphone.

11. The system of claim 9, wherein said input means includes a joystick.

12. The system of claim 9, wherein said input means includes is a speech interface.

13. The system of claim 9, wherein said first and second mobile robots each include a platform that provides three degrees of freedom.

14. The system of claim 9, further comprising a remote station that has input means for controlling said first mobile robot.

15. The system of claim 14, wherein said first mobile robot includes an arbitrator.

16. The system of claim 9, further comprising a wireless base station coupled to said first mobile robot.

17. A method for operating a mobile robot, comprising:
entering a command to move a first mobile robot through an input of a second mobile robot that is controlled by a user;
moving the first mobile robot across a floor surface;
moving together a camera and a monitor of the first mobile robot; and, moving together a camera and a monitor of the second mobile robot.

18. The method of claim 17, further comprising conducting a teleconference between the first and second mobile robots.

19. The method of claim 17, wherein entering the command is moving a joystick of the second mobile robot.

20. The method of claim 17, further comprising entering a command to move the first mobile robot from a remote station.

21. A mobile robot system, comprising:
a broadband network;
a first mobile robot with a camera and a monitor that move together in at least one degree of freedom coupled to said broadband network; and,
a second mobile robot that is coupled to said broadband network and has an input device controlled by a user to control movement of said first mobile robot across a floor surface, said second mobile robot having a camera and a monitor that move together in at least one degree of freedom.

22. The system of claim 21, wherein said first and second mobile robots each include a speaker and a microphone.

23. The system of claim 21, wherein said input device includes a joystick.

24. The system of claim 21, wherein said input device includes a speech interface.

25. The system of claim 21, wherein said first and second mobile robots each include a platform that provides three degrees of freedom.

26. The system of claim 21, further comprising a remote station that is coupled to said broadband network and has an input device to control said first mobile robot.

27. The system of claim 26, wherein said first mobile robot includes an arbitrator.

28. The system of claim 21, further comprising a wireless base station coupled to said first mobile robot and said broadband network.

29. A mobile robot system, comprising:
a broadband network;
a first mobile robot with a camera and a monitor that move together in at least one degree of freedom coupled to said broadband network; and,
a second mobile robot that is coupled to said broadband network and has input means for controlling movement of said first mobile robot across a floor surface that is controlled by a user, said second mobile robot having a camera and a monitor that move together in at least one degree of freedom.

30. The system of claim 29, wherein said first and second mobile robots each include a speaker and a microphone.

31. The system of claim 29, wherein said input means includes a joystick.

32. The system of claim 29, wherein said input means includes is a speech interface.

33. The system of claim 29, wherein said first and second mobile robots each include a platform that provides three degrees of freedom.

34. The system of claim 29, further comprising a remote station that is coupled to said broadband network and has input means for controlling said first mobile robot.

35. The system of claim 34, wherein said first mobile robot includes an arbitrator.

36. The system of claim 29, further comprising a wireless base station coupled to said first mobile robot and said broadband network.

37. A method for operating a mobile robot, comprising:
entering a command to move a first mobile robot through an input of a second mobile robot that is controlled by a user;
transmitting the command through a broadband network;
moving the first mobile robot across a floor surface;
moving together a camera and a monitor of the first mobile robot; and,
moving together a camera and a monitor of the second mobile robot.

38. The method of claim 37, further comprising conducting a teleconference between the first and second mobile robots through the broadband network.

39. The method of claim 37, wherein entering the command is moving a joystick of the second mobile robot.

40. The method of claim 37, further comprising entering a command to move the first mobile robot from a remote station, the command being transmitted through the broadband network.

* * * * *